(12) United States Patent
Bonutti

(10) Patent No.: US 9,050,152 B2
(45) Date of Patent: Jun. 9, 2015

(54) METHOD AND APPARATUS FOR USE IN OPERATING ON A BONE

(71) Applicant: Bonutti Skeletal Innovations LLC, Plano, TX (US)

(72) Inventor: Peter M. Bonutti, Effingham, IL (US)

(73) Assignee: Bonutti Skeletal Innovations LLC, Plano, TX (US)

( * ) Notice: Subject to any disclaimer, the term of this patent is extended or adjusted under 35 U.S.C. 154(b) by 0 days.

(21) Appl. No.: 14/572,980

(22) Filed: Dec. 17, 2014

(65) Prior Publication Data

US 2015/0105781 A1    Apr. 16, 2015

Related U.S. Application Data

(63) Continuation of application No. 14/445,784, filed on Jul. 29, 2014, which is a continuation of application No. 13/847,325, filed on Mar. 19, 2013, now Pat. No. 8,795,363, which is a continuation of application No.

(Continued)

(51) Int. Cl.
*A61F 2/44* (2006.01)
*A61B 17/80* (2006.01)

(52) U.S. Cl.
CPC .......... *A61B 17/8095* (2013.01); *A61B 17/8004* (2013.01)

(58) Field of Classification Search
CPC ..... A61F 2/4611; A61F 2/442; A61F 2/4455; A61F 2/2446; A61F 2/4465; A61F 2/447; A61F 2220/0025; A61F 2002/4475
See application file for complete search history.

(56) References Cited

U.S. PATENT DOCUMENTS

| 673,783 A | 5/1901 | Peters |
| 3,426,364 A | 2/1969 | Lumb |
| 3,918,100 A | 11/1975 | Shaw et al. |
| 4,298,993 A | 11/1981 | Kovaleva et al. |
| 4,344,193 A | 8/1982 | Kenny |
| 4,349,921 A | 9/1982 | Kuntz |

(Continued)

FOREIGN PATENT DOCUMENTS

| EP | 0773004 A1 | 5/1997 |
| FR | 2727003 A1 | 5/1996 |

(Continued)

OTHER PUBLICATIONS

Office Action issued Mar. 12, 2014 in U.S. Appl. No. 13/745,263 by Bonutti.

(Continued)

*Primary Examiner* — Mary Hoffman
(74) *Attorney, Agent, or Firm* — Panitch Schwarze Belisario & Nadel LLP

(57) ABSTRACT

An implantable device includes a body and a first mounting strip connected to a trailing end portion of the body. The body has a leading end portion, a first side surface, a second side surface, an upper surface, a lower surface and a central opening extending through the upper and lower surfaces. The central opening has an internal surface with an internal leading surface, a first internal side surface and a second internal side surface. A first depth is defined between the leading end and the internal leading surface, a first spacing is defined between the first side surface and the first internal side surface and a second spacing is defined between the second side surface and the second internal side surface. The first spacing is substantially the same as the second spacing.

30 Claims, 5 Drawing Sheets

Related U.S. Application Data

11/928,400, filed on Oct. 30, 2007, now Pat. No. 8,690,944, which is a continuation of application No. 10/438,705, filed on May 15, 2003, now Pat. No. 8,486,066, which is a continuation of application No. 09/566,070, filed on May 5, 2000, now Pat. No. 6,575,982, which is a continuation of application No. 09/109,126, filed on Jun. 30, 1998, now Pat. No. 6,086,593.

(56) References Cited

U.S. PATENT DOCUMENTS

| | | | |
|---|---|---|---|
| 4,385,404 | A | 5/1983 | Sully et al. |
| 4,394,370 | A | 7/1983 | Jefferies |
| 4,421,112 | A | 12/1983 | Mains et al. |
| 4,450,591 | A | 5/1984 | Rappaport |
| 4,502,161 | A | 3/1985 | Wall |
| 4,516,276 | A | 5/1985 | Mittelmeier et al. |
| 4,599,086 | A * | 7/1986 | Doty .................... 606/86 A |
| 4,713,076 | A | 12/1987 | Draenert |
| 4,772,287 | A | 9/1988 | Ray et al. |
| 4,808,185 | A | 2/1989 | Penenberg et al. |
| 4,829,152 | A | 5/1989 | Rostoker et al. |
| 4,877,020 | A | 10/1989 | Vich et al. |
| 4,880,429 | A | 11/1989 | Stone |
| 4,904,261 | A | 2/1990 | Dove et al. |
| 4,917,704 | A | 4/1990 | Frey et al. |
| 4,919,667 | A | 4/1990 | Richmond |
| 4,955,908 | A | 9/1990 | Frey et al. |
| 4,961,740 | A | 10/1990 | Ray et al. |
| 5,006,120 | A | 4/1991 | Carter |
| 5,015,255 | A | 5/1991 | Kuslich |
| 5,022,576 | A | 6/1991 | Jenq |
| 5,026,373 | A | 6/1991 | Ray et al. |
| 5,030,233 | A | 7/1991 | Ducheyne |
| 5,041,129 | A | 8/1991 | Hayhurst et al. |
| 5,053,039 | A | 10/1991 | Hofmann et al. |
| 5,061,286 | A | 10/1991 | Lyle |
| 5,108,438 | A | 4/1992 | Stone |
| 5,116,374 | A | 5/1992 | Stone |
| 5,192,327 | A | 3/1993 | Brantigan |
| 5,201,736 | A | 4/1993 | Strauss |
| 5,203,787 | A | 4/1993 | Noblitt et al. |
| 5,258,031 | A | 11/1993 | Salib et al. |
| 5,282,861 | A | 2/1994 | Kaplan |
| 5,306,309 | A | 4/1994 | Wagner et al. |
| 5,331,975 | A | 7/1994 | Bonutti |
| 5,360,450 | A | 11/1994 | Giannini |
| 5,390,683 | A | 2/1995 | Pisharodi |
| 5,397,364 | A | 3/1995 | Kozak et al. |
| 5,405,391 | A | 4/1995 | Hednerson et al. |
| 5,425,772 | A | 6/1995 | Brantigan |
| 5,443,514 | A | 8/1995 | Steffee |
| 5,458,638 | A | 10/1995 | Kuslich et al. |
| 5,458,643 | A | 10/1995 | Oka et al. |
| 5,484,437 | A | 1/1996 | Michelson |
| 5,514,180 | A | 5/1996 | Heggeness et al. |
| 5,522,899 | A * | 6/1996 | Michelson .................... 606/279 |
| 5,550,172 | A | 8/1996 | Regula et al. |
| 5,571,191 | A | 11/1996 | Fitz |
| 5,601,565 | A | 2/1997 | Huebner |
| 5,609,635 | A | 3/1997 | Michelson |
| 5,620,448 | A | 4/1997 | Puddu |
| 5,645,598 | A | 7/1997 | Brosnahan, III |
| 5,653,761 | A | 8/1997 | Pisharodi |
| 5,653,762 | A | 8/1997 | Pisharodi |
| 5,658,336 | A | 8/1997 | Pisharodi |
| 5,669,909 | A | 9/1997 | Zdeblick et al. |
| 5,683,463 | A | 11/1997 | Godefroy et al. |
| 5,683,464 | A | 11/1997 | Wagner et al. |
| 5,702,454 | A | 12/1997 | Baumgartner |
| 5,713,899 | A | 2/1998 | Marnay et al. |
| 5,716,415 | A | 2/1998 | Steffee |
| 5,722,978 | A | 3/1998 | Jenkins, Jr. |
| 5,766,251 | A | 6/1998 | Koshino |
| 5,766,252 | A | 6/1998 | Henry et al. |
| 5,769,897 | A | 6/1998 | Harle |
| 5,776,199 | A | 7/1998 | Michelson |
| 5,785,710 | A | 7/1998 | Michelson |
| 5,807,403 | A | 9/1998 | Beyar et al. |
| 5,814,084 | A | 9/1998 | Grivas et al. |
| 5,836,948 | A | 11/1998 | Zucherman et al. |
| 5,865,845 | A | 2/1999 | Thalgott |
| 5,888,223 | A | 3/1999 | Bray, Jr. |
| 5,888,224 | A | 3/1999 | Beckers et al. |
| 5,888,227 | A * | 3/1999 | Cottle ....................... 623/17.16 |
| 5,888,228 | A | 3/1999 | Knothe et al. |
| 5,895,426 | A | 4/1999 | Scarborough et al. |
| 5,904,719 | A | 5/1999 | Errico et al. |
| 5,906,616 | A | 5/1999 | Pavlov et al. |
| 5,916,267 | A | 6/1999 | Tienboon |
| 5,984,967 | A | 11/1999 | Zdeblick et al. |
| 5,989,289 | A | 11/1999 | Coates et al. |
| 6,001,099 | A | 12/1999 | Huebner |
| 6,007,580 | A | 12/1999 | Lehto et al. |
| 6,008,433 | A | 12/1999 | Stone |
| 6,042,582 | A | 3/2000 | Ray |
| 6,045,579 | A | 4/2000 | Hochshuler et al. |
| 6,066,175 | A | 5/2000 | Henderson et al. |
| 6,086,593 | A | 7/2000 | Bonutti |
| 6,099,531 | A | 8/2000 | Bonutti |
| 6,102,950 | A | 8/2000 | Vaccaro |
| 6,136,031 | A * | 10/2000 | Middleton ................. 623/17.16 |
| 6,190,414 | B1 | 2/2001 | Young et al. |
| 6,206,922 | B1 | 3/2001 | Zdeblick et al. |
| 6,206,927 | B1 | 3/2001 | Fell et al. |
| 6,241,771 | B1 | 6/2001 | Gresser et al. |
| 6,251,140 | B1 | 6/2001 | Marino et al. |
| 6,290,724 | B1 | 9/2001 | Marino |
| 6,368,325 | B1 | 4/2002 | McKinley et al. |
| 6,423,063 | B1 | 7/2002 | Bonutti |
| 6,432,106 | B1 | 8/2002 | Fraser |
| 6,458,158 | B1 | 10/2002 | Anderson et al. |
| 6,458,159 | B1 | 10/2002 | Thalgott |
| 6,471,724 | B2 | 10/2002 | Zdeblick et al. |
| 6,482,233 | B1 | 11/2002 | Aebi et al. |
| 6,575,982 | B1 | 6/2003 | Bonutti |
| 6,613,091 | B1 | 9/2003 | Zdeblick et al. |
| 6,823,871 | B2 | 11/2004 | Schmieding |
| 6,887,248 | B2 | 5/2005 | McKinley et al. |
| 6,923,810 | B1 | 8/2005 | Michelson |
| 7,001,385 | B2 | 2/2006 | Bonutti |
| 7,128,763 | B1 | 10/2006 | Blatt |
| 7,776,094 | B2 | 8/2010 | McKinley et al. |
| 8,092,537 | B2 | 1/2012 | McGahan et al. |
| 8,192,492 | B2 | 6/2012 | Robie |
| 8,470,044 | B2 | 6/2013 | Bertholet et al. |
| 8,568,484 | B2 | 10/2013 | Robie |
| 8,801,785 | B2 | 8/2014 | Brittan et al. |
| 2002/0116065 | A1 | 8/2002 | Jackson |
| 2002/0156478 | A1 | 10/2002 | Bonutti |
| 2003/0028249 | A1 | 2/2003 | Baccelli et al. |
| 2003/0199881 | A1 | 10/2003 | Bonutti |
| 2004/0148026 | A1 | 7/2004 | Bonutti |
| 2004/0153072 | A1 | 8/2004 | Bonutti |
| 2004/0254582 | A1 | 12/2004 | Bonutti |
| 2008/0046090 | A1 | 2/2008 | Paul et al. |
| 2008/0051799 | A1 | 2/2008 | Bonutti |
| 2008/0058822 | A1 | 3/2008 | Bonutti |
| 2010/0312290 | A1 | 12/2010 | McKinley et al. |

FOREIGN PATENT DOCUMENTS

| | | | |
|---|---|---|---|
| SU | 562272 | A1 | 6/1977 |
| WO | 9508306 | A1 | 3/1995 |
| WO | 9614802 | A1 | 5/1996 |
| WO | 9960837 | A2 | 12/1999 |
| WO | 9960956 | A1 | 12/1999 |
| WO | 9960957 | A1 | 12/1999 |

OTHER PUBLICATIONS

Office Action issued Apr. 11, 2014 in U.S. Appl. No. 10/755,996.
Office Action issued Aug. 18, 2014 in U.S. Appl. No. 11/928,262.

(56) References Cited

OTHER PUBLICATIONS

U.S. Appl. No. 14/445,784 by Bonutti, filed Jul. 29, 2014.
Office Action issued Oct. 2, 2014 in U.S. Appl. No. 14/445,784 by Bonutti.
Office Action issued Oct. 3, 2014 in U.S. Appl. No. 10/755,996 by Bonutti.
Office Action issued Dec. 11, 2014 in U.S. Appl. No. 14/445,784 by Bonutti.
Brochure entitled "Arthrex", "Opening Wedge Osteotomy", Copyright 1998, Arthrex Inc.
Office Action issued Dec. 13, 2005 in U.S. Appl. No. 10/438,705.
Office Action issued May 1, 2006 in U.S. Appl. No. 10/438,705.
Office Action issued Oct. 9, 2007 in U.S. Appl. No. 10/438,705.
Office Action issued May 14, 2008 in U.S. Appl. No. 10/438,705.
Office Action issued Sep. 3, 2008 in U.S. Appl. No. 10/438,705.
Office Action issued Mar. 17, 2009 in U.S. Appl. No. 10/438,705.
Office Action issued Jan. 25, 2010 in U.S. Appl. No. 10/438,705.
Office Action issued Sep. 15, 2010 in U.S. Appl. No. 10/438,705.
Office Action issued Jun. 21, 2012 in U.S. Appl. No. 10/438,705.
Office Action issued Oct. 27, 2010 in U.S. Appl. No. 11/928,400.
Office Action issued May 13, 2011 in U.S. Appl. No. 11/928,400.
Office Action issued Jun. 27, 2005 in U.S. Appl. No. 10/755,996.
Office Action issued Dec. 23, 2005 in U.S. Appl. No. 10/756,001.
Office Action issued Sep. 8, 2006 in U.S. Appl. No. 10/756,001.
Office Action issued Mar. 8, 2007 in U.S. Appl. No. 10/756,001.
Office Action issued Jul. 10, 2008 in U.S. Appl. No. 10/756,001.
Office Action issued Dec. 29, 2008 in U.S. Appl. No. 10/756,001.
Office Action issued Jun. 9, 2009 in U.S. Appl. No. 10/756,001.
Office Action issued Apr. 28, 2010 in U.S. Appl. No. 10/756,001.
Office Action issued Jun. 10, 2005 in U.S. Appl. No. 10/163,480.
Office Action issued Jan. 11, 2006 in U.S. Appl. No. 10/163,480.
Office Action issued Apr. 2, 2009 in U.S. Appl. No. 11/928,262.
Office Action issued Feb. 4, 2010 in U.S. Appl. No. 11/928,262.
Office Action issued Dec. 27, 2005 in U.S. Appl. No. 10/755,996.
Office Action issued Jul. 7, 2006 in U.S. Appl. No. 10/755,996.
Office Action issued Dec. 29, 2006 in U.S. Appl. No. 10/755,996.
Office Action issued Sep. 10, 2007 in U.S. Appl. No. 10/755,996.
Office Action issued Jan. 23, 2008 in U.S. Appl. No. 10/755,996.
Office Action issued Aug. 19, 2008 in U.S. Appl. No. 10/755,996.
Office Action issued Feb. 20, 2009 in U.S. Appl. No. 10/755,996.
Office Action issued May 10, 2010 in U.S. Appl. No. 10/755,996.
Office Action issued Nov. 21, 2011 in U.S. Appl. No. 10/755,996.
Office Action issued Jun. 13, 2012 in U.S. Appl. No. 10/755,996.
Office Action issued Mar. 12, 2007 in U.S. Appl. No. 10/755,996.
Office Action issued Jun. 27, 2005 in U.S. Appl. No. 10/756,001.
Barrett et al, "T-Fix Endoscopic Meniscal Repair: Technique and Approach to Different Types of Tears," Arthroscopy: The Journal of Arthroscopic and Related Surgery, vol. 11, No. 2, pp. 245-251 (Apr. 1995).
Cobb et al, "Late Correction of Malunited Intercondylar Humeral Fractures," The Journal of Bone and Joint Surgery, vol. 76-B, pp. 622-626 (1994).
Fellinger et al, "Radial Avulsion of the Triangular Fibrocartilage Complex in Acute Wrist Trauma: A New Technique for Arthroscopic Repair," Arthroscopy: The Journal of Arthroscopic and Related Surgery, vol. 13, No. 3, pp. 370-374 (Jun. 1997).
Hecker et al, "Pull-out strength of suture anchors for rotator cuff and Bankart lesion repairs," The American Journal of Sports Medicine, vol. 21, No. 6, pp. 874-879 (Nov.-Dec. 1993).
Hernigou et al, "Proximal Tibial Osteotomy for Osteoarthritis with Varus Deformity: A Ten to Thirteen-Year Follow-up Study," The Journal of Bone and Joint Surgery, vol. 69-A, No. 3, pp. 332-354 (Mar. 1987).
Ibarra et al, "Glenoid Replacement in Total Shoulder Arthroplastly," The Orthopedic Clinics of North America—Total Shoulder Arthroplasty, vol. 29, No. 3, pp. 403-413 (Jul. 1998).
Mosca et al, "Calcaneal Lengthening for Valgus Deformity of the Hindfoot," The Journal of Bone and Joint Surgery, vol. 77-A, No. 4, pp. 500-512 (Apr. 1995).
Murphy et al, "Radial Opening Wedge Osteotomy in Madelung's Deformity," The Journal of Hand Surgery, vol. 21A, No. 6, pp. 1035-1044 (Nov. 1996).
Unliab Surgibone—Orthopaedic Surgery, The Journal of Bone and Joint Surgery, vol. 76-B, No. 2, p. 345 (Mar. 1994).
Office Action issued Dec. 19, 2012 in U.S. Appl. No. 11/928,400.
U.S. Appl. No. 13/745,263 by Bonutti, filed Jan. 18, 2013.
Office Action issued Apr. 1, 2013 in U.S. Appl. No. 13/745,263.
Office Action issued Oct. 2, 2013 in U.S. Appl. No. 13/745,263.
Office Action issued Jan. 22, 2014 in U.S. Appl. No. 13/847,325 by Bonutti.

* cited by examiner

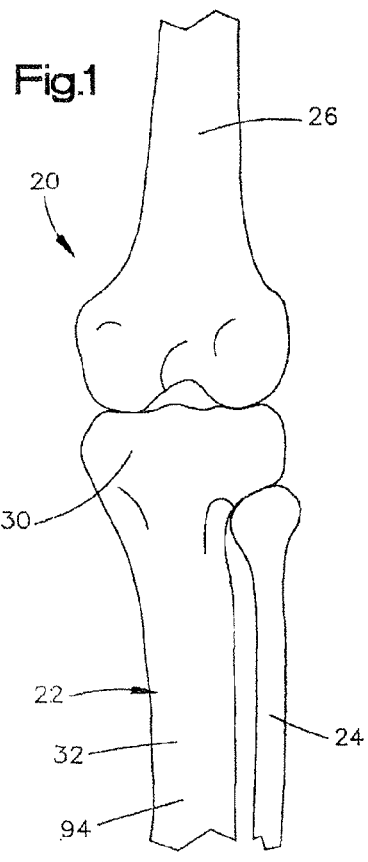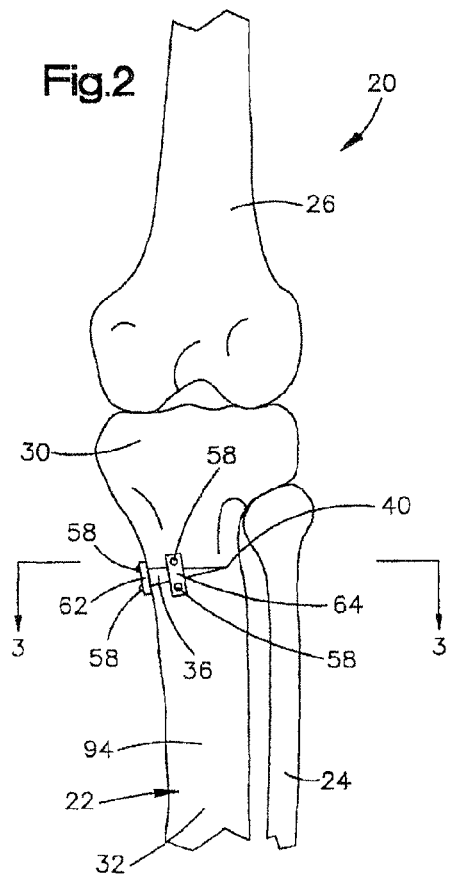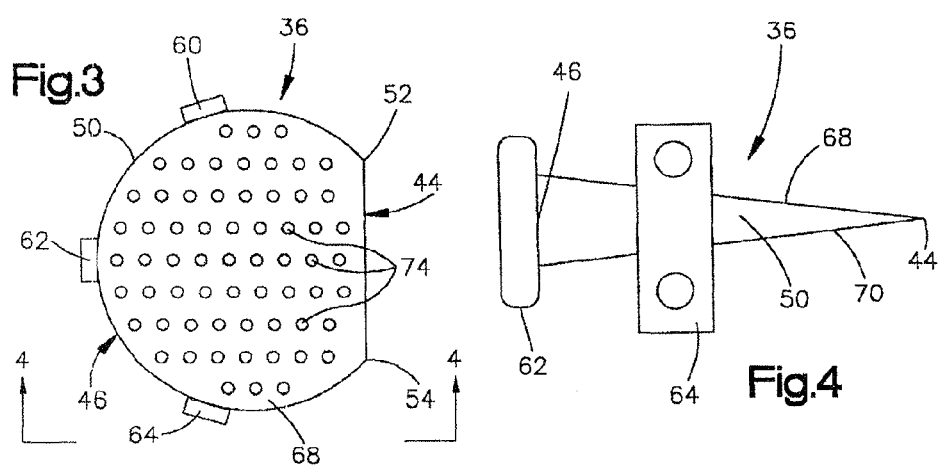

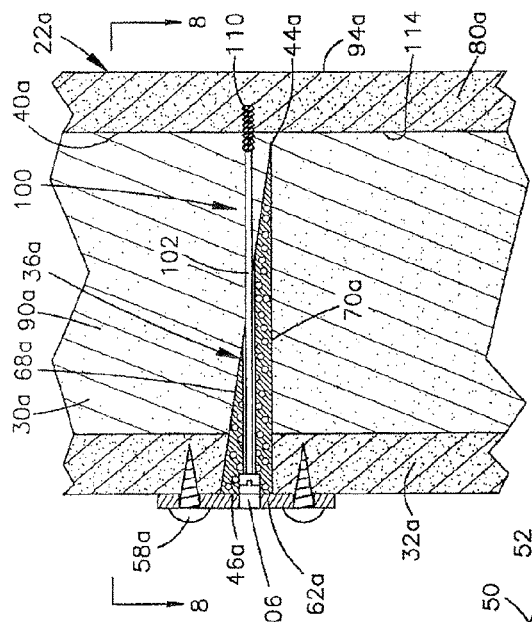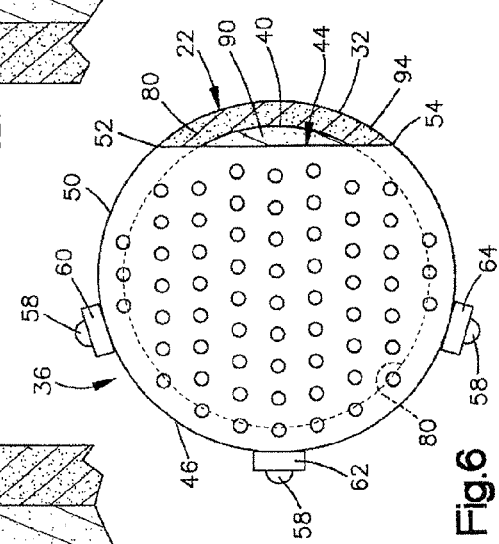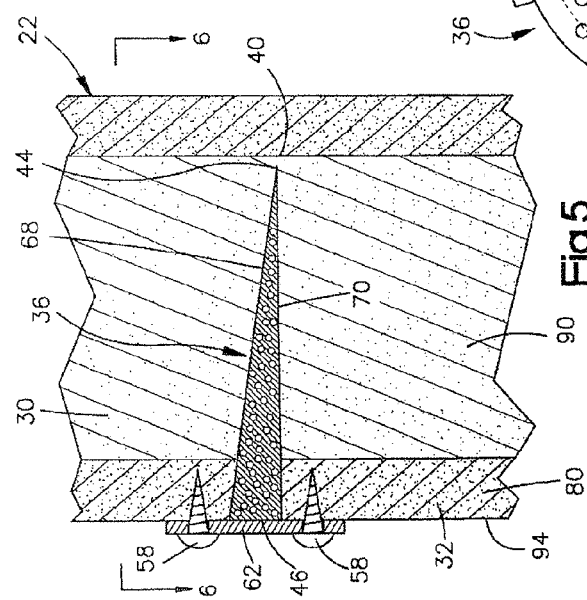

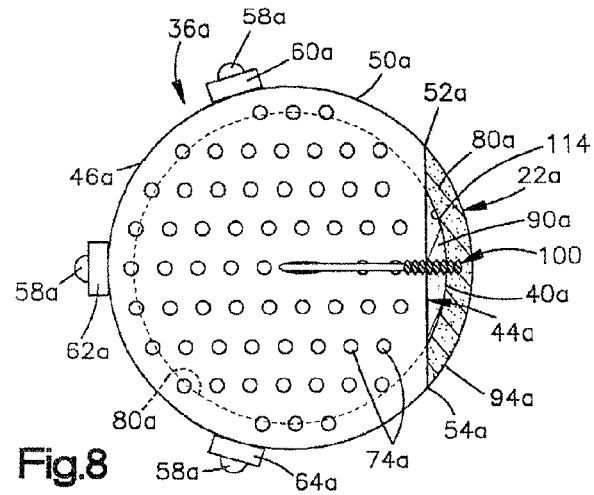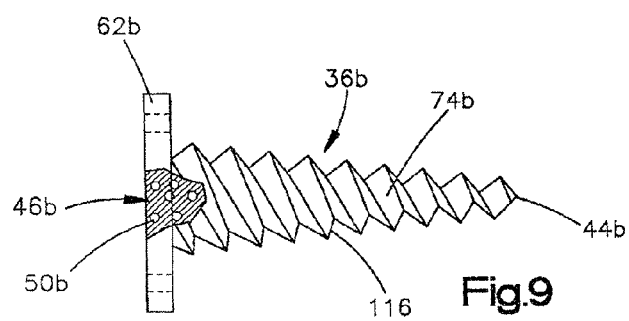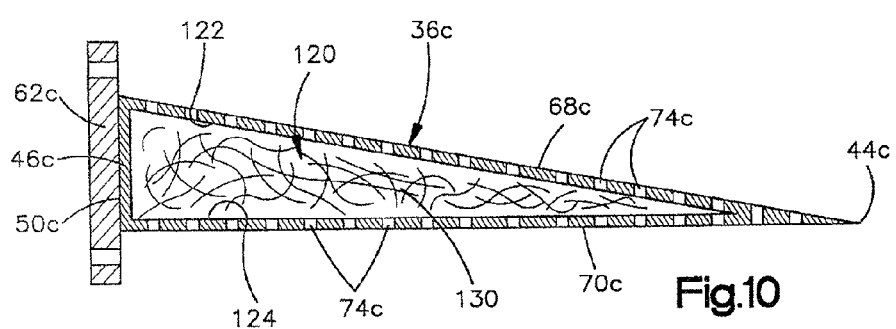

METHOD AND APPARATUS FOR USE IN OPERATING ON A BONE

CROSS-REFERENCE TO RELATED APPLICATIONS

The present application is a continuation of U.S. patent application Ser. No. 14/445,784, filed Jul. 29, 2014, which is a continuation of U.S. patent application Ser. No. 13/847,325, filed Mar. 19, 2013, now U.S. Pat. No. 8,795,363, which is a continuation of U.S. patent application Ser. No. 11/928,400, filed Oct. 30, 2007, now U.S. Pat. No. 8,690,944, which is a continuation of U.S. patent application Ser. No. 10/438,705, filed May 15, 2003, now U.S. Pat. No. 8,486,066, which is a continuation of U.S. patent application Ser. No. 09/566,070, filed May 5, 2000, now U.S. Pat. No. 6,575,982, which is a continuation of U.S. patent application Ser. No. 09/109,126, filed Jun. 30, 1998, now U.S. Pat. No. 6,086,593, the entire contents of which are incorporated herein by reference in their entirety.

BACKGROUND OF THE INVENTION

The present invention relates to a new and improved method and apparatus in which a wedge member is used to change a spatial relationship between portions of bone in a patient's body.

A known method for performing an osteotomy includes forming a slot which extends part way through a bone. A forked wedge tool is inserted into the slot. A plate is then placed in a central opening in the forked wedge tool and positioned against the so bone. The plate is secured to the bone. The forked wedge tool is then removed from the opening. This method of performing an osteotomy is disclosed in U.S. Pat. No. 5,620,448.

The foregoing osteotomy changes the spatial relationship between portions of a bone in a patient's body by forming and maintaining a wedge-shape opening in the bone. In other known methods, the spatial relationship between portions of a bone in a patient's body has been changed by removing a wedge-shape piece from the bone. The resulting opening is closed to effect the relative movement between portions of the bone. The performance of an osteotomy which includes removing a wedge-shaped piece of bone is disclosed in U.S. Pat. Nos. 5,053,039 and 5,601,565.

BRIEF SUMMARY OF THE INVENTION

The preferred present invention relates to a new and improved method and apparatus for use in changing a spatial relationship between portions of a bone in a patient's body. When this is to be done, an opening is formed in a portion of the patient's body tissue to at least partially expose the bone. Force is applied to the bone with a wedge member to move one portion of the bone relative to another portion of the bone. The wedge member may be fixedly connected with either or both portions of the bone. The opening in the patient's body is then closed with the wedge member disposed in engagement with the bone. Force can be transmitted between portions of the bone through the wedge member.

The wedge member may taper from a thick edge to a thin edge and have a side surface which extends from one end of the thin edge, along the thick edge, to the opposite end of the thin edge. The side surface of the wedge member may have a cross sectional configuration corresponding to the configuration of a portion of an outer side surface of the bone. This enables the wedge member to be aligned with the outer side surface of the bone.

The wedge member may be positioned relative to the bone at a location where a layer of hard cortical bone encloses soft cancellous bone. Opposite ends of the thin leading edge of the wedge member may be positioned in engagement with the hard cortical bone while a central portion of the thin edge of the wedge member engages the soft cancellous bone. In addition, the layer of hard cortical bone may engage the wedge member adjacent to the side surface of the wedge member.

It is contemplated that the wedge member may have many different constructions. It is believed that it will be advantageous to form the wedge member with one or more openings through which bone can grow. The wedge member may be coated with and/or contain bone growth promoting material. The wedge member may be hollow and contain material which promotes growth of bone through the wedge member.

A screw member may extend ahead of the thin leading edge of the wedge member and engage hard cortical bone. Force may be transmitted from the screw member to the wedge member to move the wedge member relative to the bone. Alternatively, the wedge member may have a circular cross sectional configuration with an external thread convolution to enable the wedge member to be moved into an opening in a bone by rotating the wedge member.

BRIEF DESCRIPTION OF THE SEVERAL VIEWS OF THE DRAWINGS

The foregoing and other features of the present invention will become more apparent upon a consideration of the following description taken in connection with the accompanying drawings wherein.

FIG. 1 is a schematic posterior illustration of the relationship between bones in a patient's body;

FIG. 2 is a schematic illustration, generally similar to FIG. 1, illustrating the manner in which a wedge member is utilized to change a spatial relationship between portions of one of the bones of FIG. 1;

FIG. 3 is an enlarged plan view, taken generally along the line 3-3 of FIG. 2, illustrating the configuration of the wedge member;

FIG. 4 is a side elevational view, taken generally along the line 4-4 of FIG. 3, further illustrating the configuration of the wedge member;

FIG. 5 is an enlarged schematic fragmentary sectional view of a portion of one of the bones of FIG. 2 and illustrating the relationship of the wedge member to the bone;

FIG. 6 is a plan view, taken generally along the line 6-6 of FIG. 5, further illustrating the relationship of the wedge member to the bone;

FIG. 7 is a schematic fragmentary sectional view, generally similar to FIG. 5, illustrating the relationship of a second embodiment of the wedge member to the bone;

FIG. 8 is a plan view, taken generally along the line 8-8 of FIG. 7, further illustrating the relationship of the wedge member to the bone;

FIG. 9 is a schematic pictorial illustration depicting the construction of a screw which forms another embodiment of the wedge member;

FIG. 10 is an enlarged sectional view of an embodiment of the wedge member of FIGS. 3-6 which is hollow and contains material to promote bone growth through the wedge member;

DETAILED DESCRIPTION OF THE INVENTION

General Description

Figure 11:
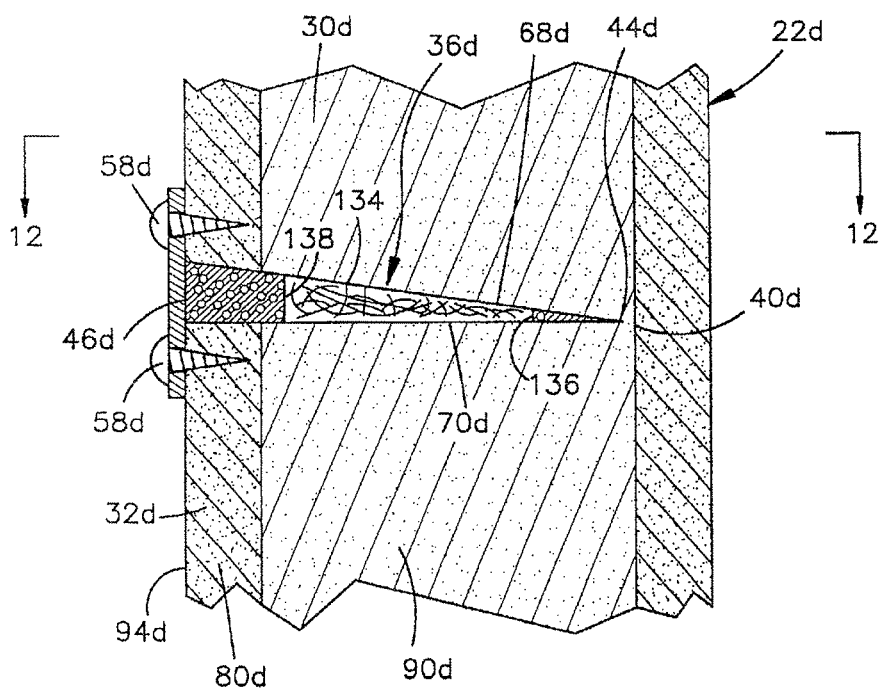
FIG. 11 is a fragmentary schematic sectional view, generally similar to FIG. 5, illustrating the relationship of another embodiment of the wedge member to the bone.

FIGS. 1 and 2 are schematic posterior illustrations of bones in a leg 20 of a patient. A tibia bone 22 and fibula bone 24 support a femur bone 26. Although bones 22, 24 and 26 in a leg of a patient have been illustrated in FIGS. 1 and 2, it should be understood that the method and apparatus of the present invention may be used in association with bones in many different portions of a patient's body.

In FIG. 1, the upper end portion 30 of the tibia bone 22 is angularly misaligned with the lower portion 32 of the tibia bone. Thus, in FIG. 1, the upper end portion 30 of the tibia bone 22 is offset in a counterclockwise direction by approximately 7 degrees from a desired orientation relative to the lower portion 32 of the tibia bone 22. In accordance with a feature of the present invention, a wedge member 36 (FIGS. 2, 3 and 4) is utilized to change the spatial relationship of the upper end portion 30 of the tibia bone 22 relative to the lower portion 32 of the tibia bone.

The wedge member 36 is formed of a relatively hard rigid material. The wedge member 36 is capable of transmitting force between the upper end portion 30 and the lower portion 32 of the tibia bone 22. This enables the leg 20 of the patient to be weight bearing as soon as the wedge member 36 is positioned in the tibia bone 22. Thereafter, bone may grow through the wedge member 36 between the upper end portion 30 and lower portion 32 of the tibia bone 22.

When the wedge member 36 is to be utilized to change the spatial relationship of the upper end portion 30 (FIG. 2) of the tibia bone 22 relative to the lower portion 32 of the tibia bone, an opening is formed in the fleshy part of the body tissue in the leg of the patient to expose the portion of the tibia bone where the wedge member is to be installed. It is contemplated that it may be preferred to install the wedge member 36 approximately two to three millimeters below the upper end of the tibia bone. The specific location where the wedge member 36 is installed will depend upon the surgeon's judgment. It is contemplated that the wedge member 36 may be installed at any one of many locations relative to a particular bone.

A saw cut is made to form a slot at the location where the wedge member 36 is to be installed. The saw cut and resulting slot extend only part way through the tibia bone 22. This results in the upper end portion 30 of the tibia bone 22 being connected with the lower portion 32 of the tibia bone by a connector or hinge portion 40 (FIG. 2) of the tibia bone.

Once a slot has been formed between the upper end portion 30 and lower portion 32 of the tibia bone, the wedge member 36 is moved into tie slot. A thin edge 44 (FIGS. 3 and 4) of the wedge member 36 is leading and a thick edge 46 of the wedge member trailing as the wedge member moves into the slot. As the wedge member 36 is forced into the slot between the upper end portion 30 and lower portion 32 of the tibia bone 22 (FIG. 2), the wedge member pivots the upper end portion of the tibia bone in a clockwise direction (as viewed in FIG. 2) relative to the lower portion of the tibia bone about an axis extending through the connector or hinge portion 40.

The wedge member 36 has an outer side surface 50 (FIGS. 3 and 4) which extends from one end 52 (FIG. 3) of the thin edge 44 of the wedge member 36 along the thick edge 46 of the wedge member to the opposite end 54 of the thin edge 44. The outer side surface 50 of the wedge member 36 has the same configuration as the outer side surface of the tibia bone 22 at the location where the saw cut formed the slot between the upper end portion 30 and lower portion 32 of the tibia bone. The outer side surface 50 of the wedge member may be formed in a plurality of sections.

Although the outer side surface 50 of the wedge member 36 has been illustrated schematically in FIG. 3 as forming a portion of a circle, it should be understood that the outer side surface 50 of the wedge member 36 will probably not have a configuration which corresponds to the configuration of a portion of a circle. The configuration of the outer side surface 50 of the wedge member 36 conforms to the cross sectional configuration of the outside surface of the bone 22 at the location where the wedge member is to be installed in the bone.

Since the outer side surface 50 of the wedge member 36 has a configuration corresponding to the configuration of the outer side surface of the bone 22 at the location where the wedge member is to be installed in the tibia bone (FIG. 2), the outer side surface 50 (FIG. 3) of the wedge member can be moved into alignment with the outer side surface of the bone 22. This enables a hard cortical outer layer of the bone 22 to engage opposite major sides of the wedge member 36 adjacent to the outer side surface 50 of the wedge member. The outer layer of hard cortical bone has continuous engagement with the wedge member 36 from the thin edge 44 to the thick edge 46 of the wedge member. This maximizes the extent of engagement of the hard outer layer of cortical bone with the wedge member 36 to avoid stress concentrations in the hard cortical outer layer.

If the wedge member 36 did not have an outer side surface 50 which extended along the outer side surface of the bone 22 from opposite sides of the hinge portion 40 of the bone, the hard cortical outer layer of bone would only be partially supported by the wedge member 36 at the slot in the bone. This would result in the load which is transmitted between the upper end portion 30 of the bone 22 and the lower portion 32 of the bone being concentrated at a relatively small area on the hard cortical outer layer of bone at the opening to the slot.

Once the wedge member 36 has been positioned relative to the bone 22, in the manner illustrated in FIG. 2, the wedge member is fixedly connected with the bone. In the illustrated embodiment of the invention, suitable screws 58 (FIG. 2) are used to fixedly connect mounting strips 60, 62 and 64 (FIG. 3) with the upper end portion 30 and lower portion 32 of the tibia bone 22. The mounting strips 60, 62 and 64 and screws 58 hold the wedge member 36 against movement relative to the bone 22 during subsequent loading of the bone by the patient.

The opening in the fleshy portion of the leg of the patient is then closed. Since the wedge member 36 has a rigid structure, the leg 20 of the patient can be load bearing immediately after closing of the opening which exposed the bone 22. With she passage of time, bone grows through the wedge member 36 between the upper end portion 30 and lower portion 32 of the bone 22.

Wedge Member

The wedge member 36 (FIGS. 3 and 4) has upper and lower major side surfaces 68 and 70 (FIG. 4). The upper and lower major side surfaces 68 and 70 slope toward each other from the thick edge 46 to the thin edge 44 of the wedge member 36. It is contemplated that a plurality of wedge members 36 having different acute angles between upper and lower major side surfaces 68 and 70 may be provided. This enables a surgeon to select a wedge member 36 having a desired thickness at the thick edge 46.

The acute angle between the flat upper and lower major side surfaces 68 and 70 is determined by the extent to which the spatial relationship between the upper end portion 30 and the lower portion 32 (FIGS. 1 and 2) of the bone 22 is to be changed by insertion of the wedge member 36. Of course, the larger the bone with which the wedge member 36 is used, the smaller is the angle between the upper and lower major side surfaces 66 and 68 to obtain a desired thickness of the wedge member at the thick edge 46 of the wedge member.

It is believed that it may be desired to have the angle between the upper and lower major side surfaces 68 and 70 be within a range between one degree and twenty degrees. Although the specific angle provided between the upper and lower major side surfaces 68 and 70 will depend upon the environment in which the wedge member is to be utilized, it is believed that the angle between the upper and lower major side surfaces 68 and 70 may frequently be between two degrees and ten degrees. It should be understood that the foregoing specific ranges of sizes for the angle between the upper and lower major side surfaces 68 and 70 have been set forth herein for purposes of clarity of description and it is contemplated that the angle between the upper and lower major side surfaces may be any one of many angles other than these specific angles.

The wedge member 36 may be formed of any one of many different known materials which are compatible with a patient's body. For example, the wedge member may be formed of human or animal bone, stainless steel, tantalum, a porous ceramic, or a polymeric material. If desired, the wedge member 36 may be formed of a biodegradable material. However, it is preferred to have the wedge member 36 formed of a rigid material which is capable of enabling the leg 20 to be weight bearing immediately after the wedge member 36 has been installed in the bone 22.

The wedge member 36 is porous so that bone can grow through the wedge member. In the illustrated embodiment of the invention, the wedge member 36 has a plurality of openings or passages 74 which extend through the wedge member between the upper and lower major side surfaces 68 and 70. The openings 74 enable bone to grow through the wedge member 36.

It is believed that it may be preferred to form the wedge member of an open cell material to provide cavities in which bone can grow through the wedge member. The wedge member 36 may have a cellular construction similar to coral. Alternatively, straight passages may be drilled or cast in the wedge member 36. It is contemplated that the wedge member 36 may be coated with a material which promotes the growth of bone. If the wedge member 36 has a cellular construction, the cells may be at least partially filled with bone growth promoting material.

When the wedge member 36 is to be inserted into the bone 22 to change the spatial relationship between the upper end portion 30 of the bone and the lower portion 32 of the bone, a location for insertion of the wedge member is selected by a surgeon. It is contemplated that it may be desired to locate the wedge member 36 approximately two to five millimeters below the upper end of the tibia bone. However, the specific location at which the wedge member is inserted into the bone 22 will be selected by the surgeon as a function of the result desired from a particular operation.

A saw slot is formed at the location where the wedge member is to be inserted into the bone. The slot extends only part way through the bone. Thus, in FIG. 2, the slot extended from the left side of the tibia bone 22 toward the right side to a location which was spaced from the right side of the tibia bone. This results in the upper end portion 30 and lower portion 32 of the bone 22 being interconnected by a connector or hinge portion 40 after the slot is formed. The thickness of the hinge portion 40 will depend upon the location where the wedge member is being installed, the extent to which the spatial relationship between portions of the bone are to be changed by insertion of the wedge member, and the physical characteristics of the bone itself.

Once the slot has been formed, with a saw or other device at a desired location in the bone, the wedge member 36 is moved into the slot. The thin edge 44 of the wedge member is easily inserted into an entry opening to the slot. Force is then applied against the thick edge 46 of the wedge member to move the wedge member further into the slot.

When the thin edge 44 of the wedge member 36 is initially positioned in the slot, the thin edge of the wedge member is diametrically opposite from the hinge portion 40 of the bone 22. A longitudinal axis of the thin edge 44, that is an axis extending between the opposite ends 52 and 54 (FIG. 3) of the thin edge, is parallel to the bottom of the slot when the thin edge is initially positioned in the slot. At this time, an axis perpendicular to the thin edge 44 and extending through the center of the wedge member 36 is aligned with an axis extending perpendicular to the bottom of inner edge of the slot and extending through the center of the bone 22.

The wedge member 36 is then moved into the slot along a linear path which extends perpendicular to the bottom or inner end of the slot and to the thin edge 44 of the wedge member. As the wedge member 36 moves into the slot along the linear path, the upper major side surface 68 (FIGS. 4 and 5) of the wedge member slides along and applies force against the upper end portion 30 of the tibia bone 22. As the wedge member 36 moves into the slot along the linear path, the lower major side surface 70 of the wedge member slides along and applies force against the lower portion 32 of the tibia bone 22. The wedge member 36 is moved into the slot under the influence of force applied against the trailing thick edge portion 46.

Although it is contemplated that the wedge member 36 could be mounted at many different locations in many different types of bone, the wedge member 36 is illustrated in FIGS. 5 and 6 as being positioned in the tibia bone 22 at a location in which an outer layer 80 of hard cortical bone extends around a core 90 of soft cancellous bone.

As the thin leading edge 44 of the wedge member 36 moves into the slot, the central portion of the thin leading edge 44 engages the outer layer 80 of hard cortical bone at the entry to the slot on a side of the bone 22 opposite from the hinge or connector portion 40. Force is applied against the outer layer 80 of hard cortical bone by the upper and lower major side surfaces 68 and 70 of the wedge member 36 at a location adjacent to the center of the opening to the slot. The force applied against the outer layer 80 of hard cortical bone by the thin leading end portion of the wedge member 36 initiates pivotal movement of the upper end portion 30 of the bone 22 about an axis extend through the hinge portion 40.

As the thin edge 44 of the wedge member moves further into the slot, the area of engagement of the thin leading edge 44 of the wedge member with the outer layer 80 of hard cortical bone moves outward from a central portion of the thin leading edge 44 toward the opposite ends 52 and 54 of the thin leading edge 44 (FIGS. 3 and 6). The upper and lower major sides 68 and 70 of the wedge member move into engagement with the layer 80 of hard cortical bone along opposite sides of the bone 22.

As the area of engagement of the thin leading edge 44 of the wedge member 36 with the outer layer 80 of hard cortical bone moves toward the opposite ends of the thin edge 44, the central portion of the thin edge 44 engages the core 90 of soft cancellous bone. When the central portion of the thin edge 44 of the wedge member 36 engages the core 90 of soft cancellous bone portions of the thin edge 44 on opposite sides of the central portion of the thin edge are in engagement with the outer layer 80 of hard cortical bone. However, depending upon the thickness and/or configuration of the outer layer 80 of hard cortical bone, the central portion of the thin edge 44 may or may not engage the core 90 of soft cancellous bone before the opposite ends 52 and 54 of the thin edge 44 of the wedge member 36 move into initial engagement with the outer layer 80 of hard cortical bone.

Continued movement of the wedge member 36 toward the bottom of the slot in the bone 22, that is, toward the right as viewed in FIGS. 5 and 6, moves the entire thin leading edge 44 of the wedge member into engagement with the core 90 of soft cancellous bone. As this occurs, the wedge member 36 moves into engagement with the outer layer 80 of hard cortical bone along opposite sides of the wedge member adjacent to the outer side surface 50 of the wedge member and adjacent to opposite sides of the bone 22. Although the thin leading edge 44 of the wedge member is in engagement with the core 90 of soft cancellous bone, the upper and lower major side surfaces 68 and 70 of the wedge member 36 are sliding along the portion of the outer layer 80 of hard cortical bone disposed behind the thin leading edge 44 of the wedge member 36, that is, to the left as viewed in FIGS. 5 and 6.

When the thin leading edge 44 of the wedge member 36 has moved rightward (as viewed in FIGS. 5 and 6) past the center of the bone 22, the opposite ends 52 and 54 or the thin leading edge again move into engagement with the outer layer 80 of hard cortical bone. Continued movement of the wedge member 36 into the slot increases the extent of engagement of the thin leading edge 44 of the wedge member with the outer layer 80 of hard cortical bone.

When the outer side surface 50 of the wedge member 36 has moved into alignment with an outer side surface 94 (FIG. 6) on the lower portion 32 of the bone 22, rightward (as viewed in FIG. 6) movement of the wedge member is interrupted. At this time, the thin leading edge 44 of the wedge member is at the bottom of the saw slot formed in the bone 22. Opposite ends 52 and 54 of the thin leading edge 44 are disposed in engagement with the outer layer 80 of hard cortical bone. The mounting strips 60, 62 and 64 are disposed in abutting engagement with the outer side surface 94 of the bone 22. Therefore, further rightward movement of the wedge member 36 into the slot is blocked and the wedge member is in the position illustrated in FIGS. 5 and 6 relative to the bone 22.

During movement of the wedge member 36 into the slot in the bone 22, in the manner previously described, the upper portion 30 of the bone pivoted relative to the lower portion 32 by force applied against the upper and lower portions of the bone by the wedge member 36. The upper end portion 30 of the bone 22 is pivoted relative to the lower portion 32 of the bone about an axis extending parallel to the thin leading edge 44 of the wedge member 36 and extending through the connector or hinge portion 40 of the bone 22.

When the outer side surface 50 on the wedge member 36 is moved into alignment with the outer side surface 94 on the bone 22, the outer side surface 50 on the wedge member 36 will form a continuation of the outer side surface 94 of the bone 22. Although perfect alignment of the outer side surface 50 of the wedge member 36 with the outer side surface 94 of the bone is desired, there may be a slight misalignment or discontinuity where the outer side surface 50 of the wedge member 36 is aligned with the outer side surface 94 of the bone 22.

In the embodiment of the wedge member 36 illustrated in FIGS. 3-6, the wedge member has been shown as being formed as a portion of a circle with the thin edge 44 being a chord of the circle. However, it is believed that it will be preferred to form the wedge member 36 with a configuration which matches the configuration of the bone 22 in which the wedge member is to be inserted. Thus, it is contemplated that the bone 22 may have an irregular outer side surface 94 which is not formed as a portion of a circle. In such a situation, the outer side surface 50 of the wedge member 36 would have a matching irregular configuration and would not be formed as a portion of a cylinder.

By having the outer side surface 50 of the wedge member 36 have a configuration which is the same as the configuration as the outer surface 94 of the bone 22, almost perfect alignment can be obtained between the wedge member 36 and the bone 22. Although there may be some misalignment of the wedge member 36 and outer side surface 94 of the bone 22, the outer layer 80 of hard cortical bone is disposed in engagement with the upper and lower major side surfaces 68 and 70 of the wedge member 36 adjacent to the outer side surface 50 of the wedge member throughout the extent of the outer side surface of the wedge member.

By providing for engagement of the outer layer 80 of hard cortical bone with the wedge member 36 throughout the extent of the opening to the slot which was formed in the bone 22, the area for transmittal of force between the upper and lower major side surfaces 68 and 70 (FIG. 5) of the wedge member and the outer layer 80 of hard cortical bone is maximized. This is because the entire extent of the outer layer 80 of cortical bone which has been cut to form the slot is disposed in engagement with the wedge member 36. The only portion of the outer layer 80 of hard cortical bone which does not engage the wedge member 36 is the portion of the outer layer of hard cortical bone which is disposed in the connector or hinge portion 40 of the tibia bone 22 (FIGS. 5 and 6). Therefore, there is no open space between surfaces on the outer layer 80 of hard cortical bone where the slot was formed. This minimizes any tendency for stress concentrations to occur due to insertion of the wedge member 36 into the bone 22.

As was previously indicated, it is desired to have almost perfect alignment of the outer side surface 50 of the wedge member 36 with the outer side 94 of the bone 22. However, the obtaining of perfect alignment of the outer side surface 50 and is the wedge member 36 with the outer side surface 94 on the bone 22 will be difficult due to the fact that bones on different patients do not have exactly the same configuration. In addition, the obtaining of perfect alignment between the outer side surface 50 of the wedge member 36 and the outer side surface 94 of the bone 22 is made difficult due to the fact that the configuration of the outer side surface 94 of the bone 22 varies along the extent of the bone.

The outer side surface 50 of the wedge member 36 is considered as being aligned with the outer side surface 94 of the bone 22 when there is a slight discontinuity between the outer side surface 94 of the bone and the outer side surface 50 of the wedge member 36. However, the extent of this discontinuity should be minimized. Close alignment of the outer side surface 50 of the wedge member 36 with the surface 94 on the bone 22 maximizes the extent of engagement of the outer layer 80 of hard cortical bone with the wedge member. In addition, close alignment of the outer side surface 50 of the wedge member 36 with the surface 94 on the bone 22 minimizes the extent to which the wedge member projects outward from the outer side surface of the bone.

Once the wedge member 36 has been positioned relative to the bone 22, in the manner previously explained, the screws 58 are used to fixedly connect the wedge member 36 with the upper end portion 30 and lower portion 32 of the bone 22. The screws 58 engage the outer layer of hard cortical bone (FIG. 5) to hold the wedge member 36 against movement relative to the borne 22. It is contemplated that the wedge member 36 could be connected with the bone 22 in a manner other than by using screws 58.

Since the wedge member 36 is rigid, it can immediately transmit loads between the upper end portion 30 and lower portion 32 of the tibia bone 22. Therefore, after the incision which exposed the site at which the wedge member 36 is inserted into the bone 22 has been closed, the patient can begin to apply weight to the leg 20. This weight will be transmitted through the entire extent of the outer layer 80 of hard cortical bone. Thus, the portion of the outer layer 80 of hard cortical bone in the connector or hinge portion 40 of the tibia bone 22 is not severed and can transmit force in the usual manner. The portion of the outer layer 80 of hard cortical bone which was cut to form the slot into which the wedge 36 was inserted, engages the upper and lower major side surfaces 68 and 70 of the wedge member 36. Since the wedge member 36 is rigid, force can be transmitted between the portions of the outer layer 80 of hard cortical bone which engage the wedge member.

The central portion of the wedge member 36 engages the core 90 of soft cancellous bone. Since the wedge member 36 is porous, the soft cancellous bone can grow through openings formed in the wedge member 36 to fuse the upper end portion 30 and lower portion 32 of the bone 22. The growth of the soft cancellous bone through the wedge member 36 may be promoted by coating the wedge member with known bone growth inducing substances. In addition, it is believed that the hard cortical bone of the outer layer 80 will eventually grow through openings 74 in the wedge member 36. The openings 74, which extend through the wedge member 36, may have a straight cylindrical configuration or may have an irregular configuration, similar to the configuration of openings or cavities formed in natural coral.

In the illustrations of FIGS. 5 and 6, the wedge member 36 is positioned in bone 22 at a location where an outer layer 80 of hard cortical bone extends around a core 90 of soft cancellous bone. However, the wedge member 36 could be used at locations where one or both major side surfaces 68 and 70 are engaged by only hard cortical bone. Although the wedge member 36 has been illustrated in FIG. 2 being used in a bone 22 in a patient's leg 20, the wedge member could be used with other bones. For example, the wedge member 36 could be used in association with bones in a patient's arm, wrist, hand, ankle or foot.

In the embodiment of the invention illustrated in FIGS. 2-6, the openings 74a are provided in the wedge member 36a to enable bone to grow through the wedge member. If desired, the openings 74a could be omitted.

Wedge Member

Second Embodiment

In the embodiment of the wedge member 36 illustrated in FIGS. 2-6, the wedge member is pushed into a slot formed in the bone 22 by the application of force against the thick edge 46 of the wedge member. In the embodiment of the invention illustrated in FIGS. 7 and 8, a long thin screw member is utilized to guide at least a portion of the movement of the wedge member into the bone and to apply force to the wedge member to pull the wedge member into the slot formed in the bone. Since the embodiment of the invention illustrated in FIGS. 7 and 8 is generally similar to the embodiment of the invention illustrated in FIGS. 2-6, similar numerals will be utilized to designate similar components, the suffix letter "a" being associated with the numerals of FIGS. 7 and 8 to avoid confusion.

A wedge member 36a is inserted into a bone 22a to change the spatial relationship of an upper portion 30a (FIG. 7) of the bone relative to a lower portion 32a of the bone. The wedge member 36a has a thin edge 44a and a thick edge 46a. An outer side surface 50a (FIG. 8) extends between opposite ends 52a and 54a of the thin edge 44a (FIG. 8). Upper and lower major side surfaces 68a and 70a (FIG. 7) extend between the thin edge 44a and the thick edge 46a. The flat upper and lower major side surfaces 68a and 70a are skewed at an acute angle relative to each other.

Openings 74a (FIG. 8) extend through the wedge member 36a to enable bone to grow through the wedge member. The opening 74a may have a straight cylindrical configuration or may have an irregular configuration, similar to openings formed in natural coral. The wedge member 36a may be coated with bone growth promoting material and/or the openings 74a filled with bone growth promoting material. If desired, the openings 74a may be omitted.

A plurality of mounting strips 60a, 62a and 64a (FIG. 8) engage an outer side surface 94a of the bone 22a. Suitable fasteners 58a connect the wedge member 36a with the bone 22a. The outer side surface 50a or the wedge member 36a is aligned with the outer side surface 94a of the bone 22a.

The wedge member 36a has the same general construction as the wedge member 36 of FIGS. 1-6. The wedge member 36a is inserted into a slot formed in the bone 22a in much the same manner as previously described in connection with the embodiment of the invention illustrated in FIGS. 1-6. However, in accordance with a feature of the embodiment of the invention illustrated in FIGS. 7 and 8, a screw member 100 is utilized to guide movement of the wedge member 36a relative to the bone 22a and to apply force to the wedge member 36a to pull the wedge member into a slot formed in the bone 22a.

The screw member 100 has a straight elongated shank 102 (FIG. 7) which extends through the wedge member 36a. A head end portion 104 of the screw member 100 is fixedly connected with the shank 102 and disposed in a suitable recess formed in the wedge member 36a. An opening 106 is formed in the mounting strip 62a to provide access to the head end portion 104 of the screw member 100.

The screw member 100 has en externally threaded end portion 110 disposed on the end of the shank 102 opposite from the head end portion 104. The externally threaded end 110 of the screw member 100 is engageable with the outer layer 80a of hard cortical bone at the hinge or connector section 40a of the bone 22a.

When the wedge member 36a is to be inserted into a slot in the bone 22a, the wedge member 36a is moved into the slot in the manner previously explained in conjunction with the embodiment of the invention illustrated in FIGS. 2-6. As the wedge member 36a approaches the position shown in FIG. 7, the externally threaded end 110 of the screw member 100 engages an inner side surface 114 of the outer layer 80a of hard cortical bone. The head end portion 104 of the screw member 100 is then rotated. This causes the externally threaded end portion 110 of the screw member to move into threaded engagement with the outer layer 80a of hard cortical bone.

Continued rotation of the screw member 100 results in the head end portion 104 applying force against the wedge member 36a to pull the wedge member toward the right (as viewed in FIG. 7). As the wedge member 36a is pulled toward the right by force transmitted from the screw member 100 to the wedge member, the mounting strips 60a, 62a and 64a (FIG. 8) move into abutting engagement with the outer side surface 94a on the bone 22a. The shank 102 of the screw member 100 guides movement of the wedge member 36a relative to the bone 22a. Rotation of the screw member 100 and movement of the wedge member 36a toward the right (as viewed in FIG. 7) is then interrupted. The mounting strips 60a, 62a, and 64a are fixedly connected with the upper end portion 30a and lower portion 32a of the bone 22a by fasteners (screws) 58a.

Although the wedge member 36a has been illustrated in FIGS. 7 and 8 at a location where a layer 80a of hard cortical bone encloses a core 90a of soft cancellous bone, the wedge member 36a could be used at a location where the wedge member engages only hard cortical bone. Although it is preferred to provide the openings 74a to enable bone to grow through the wedge member 36a, the openings may be omitted if desired.

Wedge Member

Third Embodiment

In the embodiment of the wedge member illustrated in FIGS. 2-8, the wedge member has flat major side surfaces which extend from a relatively thick edge 46 of the wedge member to a relatively thin edge 44 of the wedge member. In the embodiment of the invention illustrated in FIG. 9, the wedge member is formed as an axially tapered screw. Since the wedge member of the embodiment of the invention illustrated in FIG. 9 changes the spatial relationship between end portions of a bone in a patient's body in a manner similar to that explained in conjunction with the embodiments of the invention illustrated in FIGS. 2-7, similar numerals will be utilized to identify components of the embodiment of the invention illustrated in FIG. 9, the suffix letter "b" being associated with the numerals of FIG. 9 to avoid confusion.

A wedge member 36b has a thin edge or point 44b and a thick edge or head 46b (FIG. 9). A mounting strip 62b is connected with the thick edge 46b and engages an outer side surface of a bone to limit movement of the wedge member 36b relative to the bone. A side surface 50b on the thick edge 46b of the wedge member 36b is aligned with an outer side surface of the bone when the mounting strip 62b engages the outer side surface of the bone.

In accordance with a feature of this embodiment of the invention, the wedge member 36b has a spiral external thread convolution 116. The thread convolution 116 has a generally conical configuration and tapers from the thick edge 50b of the wedge member 36b to the thin edge or point 44b of the wedge member 36b.

When the wedge member 36b is to be inserted into a bone, a slot is formed in the bone in the same manner as previously explained in conjunction with the embodiment of the invention illustrated in FIGS. 2-8. The wedge member 36b is then screwed into the slot. In order to screw the wedge member 36b into the slot, force may be applied to the mounting strip 62b to rotate the wedge member 36b about its longitudinal central axis. Alternatively, a socket may be provided in the thick edge 46b to receive a suitable tool which transmits torque to the wedge member 36b.

As this occurs, the external thread convolution 116 on the wedge member 36b cooperates with the hard cancellous outer layer of the bone to effect axial movement of the wedge member into the slot in the bone. As the wedge member 36b enters the slot in the bone, the portion of the bone, corresponding to the upper end portion 30 of FIG. 2, pivots relative to a lower portion 32. This results in a change in the spatial relationship between the upper portion and lower portion of the bone.

Prior to moving the wedge member 36b into the slot in the bone, a longitudinal central axis of the wedge member is aligned with an axis which is perpendicular to a bottom of the slot and extends through the center of the bone. The wedge member 36b is then rotated about its longitudinal central axis. As the wedge member 36b rotates and moves into the slot, the wedge member moves along a straight path which extends perpendicular to an axis about which the upper end portion of the bone is pivoted relative to the lower portion of the bone. Movement of the wedge member 36b into the slot is interrupted with the thin edge or point 44b spaced from a connector or hinge portion of the bone which interconnects the upper end portion and lower portion of the bone.

A plurality of openings 74b are formed in the wedge member 36b to enable bone to grow through the wedge member in the manner previously explained in conjunction with the embodiment of FIGS. 1-8. The wedge member 36b is coated with a bone growth promoting material. The wedge member 36b may be hollow to provide a cavity to hold bone growth promoting material.

Wedge Member

Fourth Embodiment

An the embodiment of the invention illustrated in FIGS. 2-9, the wedge member has openings to enable bone to grow through the wedge member. In the embodiment of the invention illustrated in FIG. 10, the wedge member is hollow to provide a cavity which holds bone growth promoting material. Since the embodiment of the invention illustrated in FIG. 10 is generally similar to the embodiment of the invention illustrated in FIGS. 2-9, similar numerals will be utilized to designate similar components, the suffix letter "c" being associated with the embodiment of FIG. 10 to avoid confusion.

A wedge member 36c (FIG. 10.) has a thin edge 44c and a thick edge 46c. An outer side surface 50c extends between opposite ends of the thin edge 44c in the same manner as is illustrated in FIGS. 3 and 6 for the embodiment of the invention of FIGS. 2-6. The wedge member 36c has the same overall configuration as the wedge member 36 of FIGS. 2-6.

A mounting strip 62c is connected with the thick edge 44c of the wedge member 36c. Additional mounting strips, corresponding to the mounting strips 60 and 64 of the embodiment of the invention illustrated in FIGS. 3 and 6, are provided on the wedge member 36c. When the outer side surface 50c on the wedge member 36c has moved into alignment with the outer side surface of the bone, the mounting strip 62c engages the outer side surface of the bone. Suitable fasteners may be used to interconnect the bone and the mounting strip 62c. Although only a single mounting strip 62c has been illustrated in FIG. 10, it should be understood that additional mounting strips, corresponding to the mounting strips 62 and 64 of FIG. 3, are associated with the wedge member 36c.

The wedge member 36c has a flat upper major side surface 68c and a flat lower major side surface 70c. The upper and lower major side surfaces 68c and 70c have the same configuration as the upper and lower major side surfaces 68 and 70 of the embodiment of the invention illustrated in FIGS. 2-6. The outer side surface 50c has the same configuration as the outer side surface 50 of the embodiment of the invention illustrated in FIGS. 2-6. The upper and lower major side surfaces 68c and 70c (FIG. 10) are disposed at an acute angle and taper from the thick edge 46c to the thin edge 44c of the wedge member 36c.

The wedge member 36c is rigid to enable it to be weight bearing as soon as it is positioned in a bone. Although the wedge member 36c could be formed of many different materials, it is formed of stainless steel.

In accordance with a feature of this embodiment of the invention, the wedge member 36c (FIG. 10) is hollow. Therefore, a compartment or cavity 120 is formed in the wedge member 36c. The compartment 120 has upper and lower inner side surfaces 122 and 124 which are smaller than the upper and lower major side surfaces 68c and 70c of the wedge member 36c. However, the inner side surfaces 122 and 124 of the compartment 120 have the same general configuration as the upper and lower major side surfacers 68c and 70c of the wedge member 36c.

The compartment 120 is filled with a bone growth inducing material 130. The bone growth inducing material 130 is (not shown) formed in either the upper major side surface 68c or the lower major side surface 70c of the wedge member 36c. Once the compartment 120 has been filled with the bone growth inducing material 130, the opening to the compartment is closed. However, openings 74c in the wedge member 36c enable bone to grow through the wedge member.

The growth of bone through the wedge member 36c is promoted by the bone growth inducing material 130 in the compartment 120. The bone growth inducing material 130 in the compartment 120 may be any one of many known compositions. For example, apatite compositions with collagen may be utilized. Demineralized bone powder may also be utilized. Regardless of which of the known bone growth inducing materials are selected, the presence of the bone growth inducing material in the compartment 120 will promote a growth of bone through the openings 74c in the wedge member 36c.

The wedge member 36c may, itself, be formed of a suitable rigid material, such as tantalum or stainless steel. In addition to the bone growth inducing material 130 in the compartment 120, the surfaces of the wedge member 36c and the openings 74c may be coated with suitable bone growth inducing materials. Although the wedge member 36c has been shown as having straight cylindrical openings 74c through which bone grows, the wedge member 360 could have an open celled construction if desired.

Wedge Member

Fifth Embodiment

Figure 12:
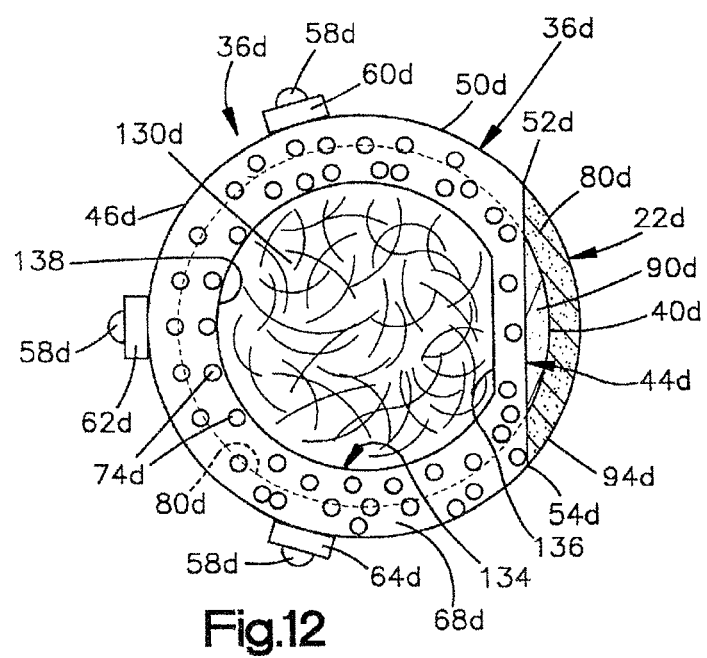
FIG. 12 is a plan view, taken generally along the line 12-12 of FIG. 11 and illustrating the configuration of an opening extending through the wedge member of FIG. 11.

In the embodiment of the invention illustrated in FIGS. 2-10, a plurality of relatively small openings 74 extend through the various wedge members to enable bone to grow through the wedge members. In the embodiment of the invention illustrated in FIGS. 11 and 12, a relatively large central opening is provided in the wedge member to enable bone to grow through the wedge member. Since the embodiment of the invention illustrated in FIGS. 11 and 12 is generally similar to the embodiment of the invention illustrated in FIGS. 2-10, similar numerals will be utilized to designate similar components, the suffix letter "d" being associated with the numerals of FIGS. 11 and 12 to avoid confusion.

A wedge member 36d (FIGS. 11 and 12) has a thin edge 44d and a thick edge 46d. An outer side surface 50d extends between opposite ends 52d and 54d (FIG. 12) of the thin edge 44d. The outer side surface 50d has a configuration which corresponds to the configuration of an outer side surface 94d of a bone 22d (FIG. 11). The wedge member 36d has flat upper and lower major side surfaces 68d and 70d which are skewed at an acute angle relative to each other and extend between the thin edge 44d and the thick edge 46d of the wedge member 36d.

The wedge member 36d has the same overall configuration as the wedge member 36 of the embodiment of the invention illustrated in FIGS. 2-6. Thus, the side surface 50d (FIG. 12) has the same configuration as the side surface 50 of FIGS. 3 and 4. The upper and lower major side surfaces 68d and 70d (FIGS. 11 and 12) have outer edge portions with the same configuration as the outer edge portion of the major side surfaces 68 and 70 of FIGS. 3 and 4.

When the wedge member 36d has been inserted into a slot formed in a bone in the manner previously explained in conjunction with the embodiment of the invention illustrated in FIGS. 2-6, mounting strips 60d, 62d, and 64d on the wedge member 36d move into abutting engagement with the outer side surface 94d of the bone 22d (FIG. 17). The mounting strips 60d, 62d, and 64d are fixedly connected with the upper end portion 30d and lower portion 32d of the bone 22d by suitable fasteners 58d. The fasteners 58d retain the wedge member 36d against movement from a position in which the side surface 50d is aligned with the outer side surface 94d of the bone 22d.

As the wedge member 36d is inserted into the slot in the bone 22d, an upper portion 30d (FIG. 11) of the bone 22d is pivoted relative to a lower portion 32d to change the spatial relationship between the upper portion 30d and lower portion 32d of the bone 22d. The upper portion 30d of the bone 22d pivots about an axis which extends parallel to the thin edge 44d of the wedge member 36d. The axis about which the upper portion 30d of the bone pivots extends through the hinge or connector portion 40d of the bone 22d and is parallel to the bottom of the slot formed in the bone 22d to receive the wedge member 36d.

In accordance with a feature of the present invention, the wedge member 36d has a large central opening 134 through which bone may grow. The openings 134 extends between upper and lower major side surfaces 68d and 70d of the wedge member 36d. The opening 134 is configured in such a manner that the upper and lower major side surfaces 68d and 70d of the wedge member 36d engage an outer layer 80d of hard cortical bone throughout movement of the wedge member 36d into the slot formed in the bone 22d.

When the wedge member 36d has moved into the bone 22d, to the position shown in FIGS. 11 and 12, the large opening 134 enables the core 90d of soft cancellous bone to easily grow through the wedge member 36d. If desired, material 130d (FIG. 11) for promoting a growth of bone could be positioned in the opening 134. At this time, the outer layer 80d of hard cortical bone is disposed in abutting engagement with opposite major side surfaces 68d and 70d on the wedge member 36d throughout the extent of the opening to the slot into which the wedge member is inserted. Relatively small openings 74d are provided in the wedge member 36d to enable hard cortical bone to grow through the wedge member.

The opening 134 has a configuration which is similar to but smaller than the overall configuration of the wedge member 36d. Thus, the opening 134 has a flat, rectangular side surface 136 which extends parallel to the thin edge 44d of the wedge member 36d. The opening 134 has an arcuate side surface 138 which is spaced substantially the same distance from the outer side surface 50d throughout the extent of the side surface 138 of the opening 134 and the side surface 50d of the wedge member 36d.

The side surface 138 of the opening 134 is spaced from the outer side surface 50d by a distance which is greater than the thickness of the outer layer 80d of hard cortical bone. Therefore, as the wedge member 36d is inserted into the slot formed in the bone 22d, the outer layer 80d of hard cortical bone engages the upper and lower major side surfaces 58d and 70d of the wedge member 36d. The outer layer 80d of hard cortical bone is in engagement with the upper and lower major side surfaces 68d and 70d of the wedge member 36d when the outer side surface 50d of the wedge member is aligned with the outer side surface 94d of the bone 22d. The outer layer 80d of hard cortical bone is disposed in engagement with the wedge member 36d throughout the extent of the opening to the slot into which the wedge member 36d is inserted.

When the wedge member 36d has been moved into the slot formed in the bone 20d, the mounting strips 60d, 62d and 64d move into abutting engagement with the outer side surface 94d of the bone. Suitable fasteners 58d can then be utilized to connect the wedge member 36d with the upper end portion 30d and the lower portion 32d of the bone 22d. The fasteners 58d maintain the outer side surface 50d on the wedge member 36d in alignment with the outer side surface 94d of the bone 22d.

The wedge member 36d can, upon being positioned relative to the bone and an incision which was made to expose the bone closed, be load bearing. This is because the outer layer 80d of hard cortical bone extends through the hinge portion 40d and can support a load in the usual manner. The outer layer 80d of hard cortical bone is disposed in engagement with the upper and lower major side surfaces 68d and 70d of the rigid wedge member 36d at a location offset to the left (as viewed in FIG. 12) from the hinge on connector portion 40d. Therefore, force can be transmitted between the upper end portion 30d and lower portion 32d (FIG. 11) through the wedge member 36d as soon as the wedge member has been properly installed in the bone 22d.

With the passage of time, the soft cancellous bone 90d grows through and completely fills the opening 134 in the wedge member 36d. Although one specific opening configuration has been illustrated in FIG. 12, it is contemplated that the opening 134 could have any desired configuration. In addition to the bone growth promoting material 130d, the wedge member 36d could be coated with bone growth promoting material. If desired, the small openings 74d could be omitted.

Wedge Member

Fifth Embodiment

In the embodiment of the invention illustrated in FIGS. 1-6, the wedge member has flat major side surfaces. In the embodiment of the invention illustrated in FIGS. 13 and 14, the wedge member has major side surfaces with a stepped configuration. Since the embodiment of the invention illustrated in FIGS. 13 and 14 is generally similar to the embodiment of the invention illustrated in FIGS. 2-6, similar numerals will be utilized to identify similar components, the suffix letter "e" being associated with the numerals of FIGS. 13 and 14 to avoid confusion.

Figure 13:
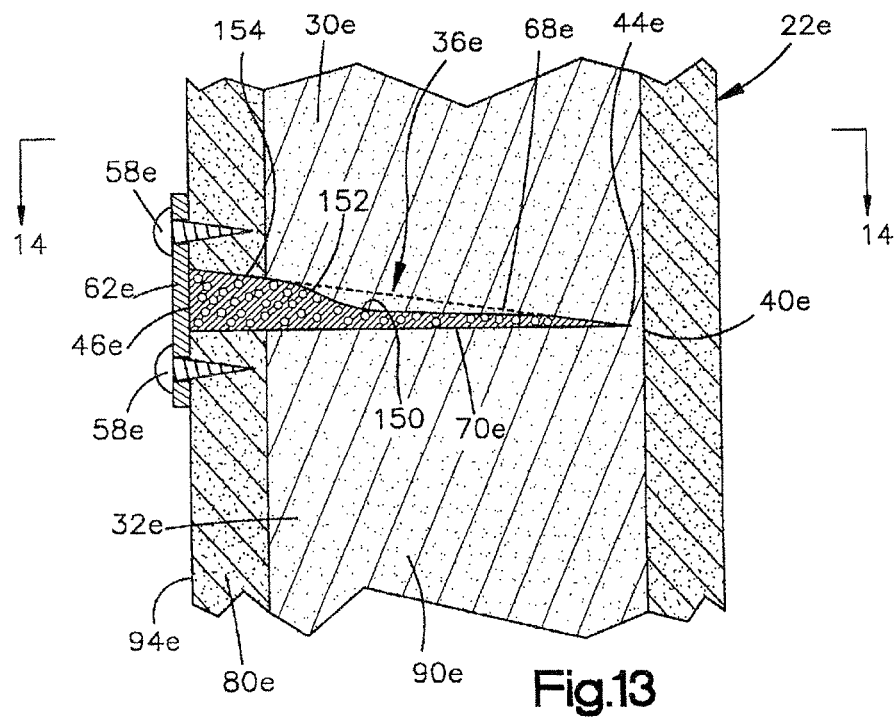
FIG. 13 is a schematic fragmentary sectional view, similar to FIGS. 5, 7 and 11, illustrating the relationship of a stepped wedge member to a bone.
Figure 14:
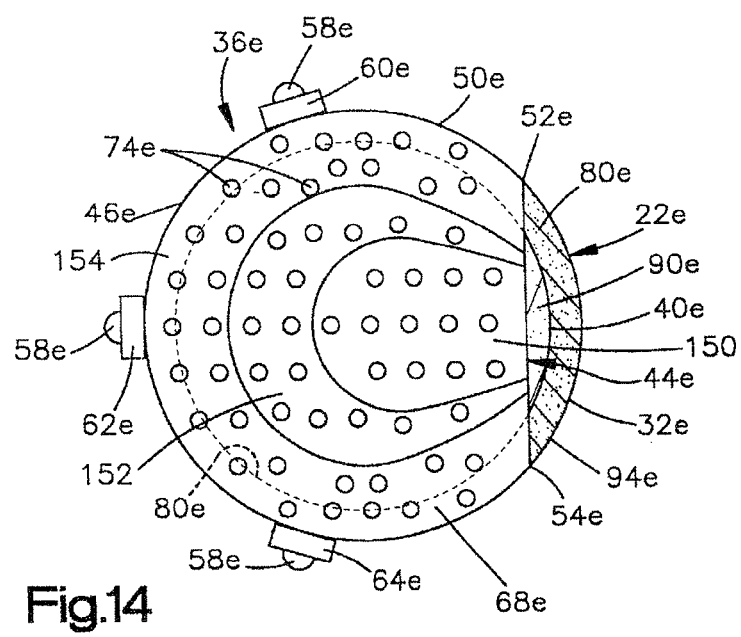
FIG. 14 is a plan view, taken generally along the line 14-14 of FIG. 13, further illustrating the configuration of the stepped wedge member.

A wedge member 36e is used to change a spatial relationship between an upper end portion 30e and a lower portion 32e of a bone 22e (FIG. 13). The wedge member 36e includes a thin edge 44e and a thick edge 46e. The wedge member 36e has an outer side surface 50e which extends between opposite ends 52e and 54e (FIG. 14) of the thin edge 44e. The wedge member 36e has ant upper major side 68e (FIG. 13) and a lower major side 70e.

A plurality of mounting strips 60e, 62e and 64e move into abutting engagement with an outer side surface 94e of the bone 22e when the wedge member 36e is inserted into a slot formed in the bone in the manner previously explained. As the wedge member 36e is inserted in to the slot in the bone, the upper end portion 30e of the bone 22e pivots about an axis which extends through a connector or hinge portion 40e of the bone. The axis about which the upper portion 30e of the bone pivots extends parallel to the thin edge 44e of the wedge member 36e.

When the mounting strips 60e, 62e and 64e have moved into abutting engagement with the outer side surface 94e of the bone 22e, the outer side surface 50e is in alignment with the outer side surface 94e of the bone 22e. Suitable fasteners 58e are utilized to connect the wedge member 46e with the upper end portion 30e and lower portion 32e of the bone 22e in the manner previously explained.

In accordance with a feature of this embodiment of the invention, the upper major side 68e of the wedge member 36e has a stepped configuration. Thus, the upper major side 68e of the wedge member 36e includes a flat surface area 150 (FIGS. 13 and 14) which extends at a first, relatively small acute angle relative to the lower major side surface 70e of the wedge member 36e. A second surface area 152 extends from the surface area 150 toward the outer side surface 50e of the wedge member 36e at a second acute angle relative to the lower side surface 70e. The second acute angle, at which the side surface 152 extends relative to the lower side surface 70e (FIG. 13), is greater than the first angle at which the side surface area 150 extends relative to the lower side surface 70e.

Finally, the wedge member 36e includes a surface area 154 which extends outward from the surface area 152 to the outer side surface 50e of the wedge member 36e. The surface 154 slopes at an acute angle relative to the lower side surface 70e of the wedge member 36e. The angle which the surface 154 makes with the dower side surface 70e is greater than the angle which the surface area 150 makes with the lower side surface 70e. The angle which the surface area 150 makes with the lower side surface 70e of the wedge member 36e is less than the angle which the surface area 152 makes with the lower side surface 70e (FIG. 13).

The surface area 154 extends a substantially constant distance from the outer side surface 50e of the wedge member 36e throughout the extent of the surface area 154 (FIG. 14). Since the surface area 152 extends between the surface area 150 and the surface area 154 (FIG. 14) the extent of the surface area 152 varies as a function of the distance of the surface area from a perpendicular to the thin edge 44e and through the center of wedge member 36e. The resulting stepped configuration of the wedge member 36e facilitates initial movement of the wedge member into the slot formed in the bone 22e.

A plurality of openings 74e extend through the wedge member 36e. The openings 74e enable bone to grow through the wedge member 36e The openings 74e may have a straight cylindrical configuration or may have an open-celled structure. The wedge member 36e may be coated with bone growth promoting material and/or the openings 74e may be at least partially filled with bone growth promoting material.

An outer layer 80e of hard cortical bone is disposed in engagement with the surface area 154 adjacent to the outer side surface 50e of the wedge member 36e. The portion of the outer layer 80e of hard cortical bone exposed by formation of the slot in the bone also engages the lower major side surface 70e of the wedge member 36e. The wedge member 36e is formed of a rigid material which is capable of transmitting force between the upper end portion 30e and the lower portion 32e of the bone 22e. Therefore, the bone is immediately weight supporting when the wedge member 36e is positioned in the bone in the manner illustrated in FIGS. 13 and 14.

CONCLUSION

In view of the foregoing description, it is apparent that the present invention provides a new and improved method and apparatus for use in changing a spatial relationship between portions of a bone 22 in a patient's body. When this is to be done, an opening is formed in a portion of the patient's body tissue to at least partially expose the bone 22. Force is applied to the bone 22 with a wedge member 36 to move one portion 30 of the bone relative to another portion 32 of the bone. The wedge member 36 may be fixedly connected with either or both portions of the bone. The opening in the patient's body is then closed with the wedge member 36 disposed in engagement with the bone 22. Force can be transmitted between portions 30 and 32 of the bone 22 through the wedge member 36.

The wedge member 36 may taper from a thick edge 46 to a thin edge 44 and have a side surface 50 which extends from one end 52 of the thin edge, along the thick edge, to the opposite end 54 of the thin edge. The side surface 50 of the wedge member 36 has a cross sectional configuration corresponding to the configuration of a portion of an outer side surface 94 of the bone 22. This enables the wedge member 36 to be aligned with the outer side surface 94 of the bone 22.

The wedge member 36 may be positioned relative to the bone 22 at a location where a layer 80 of hard cortical bone encloses soft cancellous bone 90. Opposite ends 52 and 54 of the thin edge 44 of the wedge member 36 may be positioned in engagement with the hard cortical bone 80 while a central portion of the thin edge 44 of the wedge member 36 engages the soft cancellous bone. In addition, the layer 80 of hard cortical bone may engage the wedge member 36 adjacent to the side surface 50 of the wedge member.

It is contemplated that the wedge member 36 may have many different constructions. It is believed that it will be advantageous to form the wedge member 36 with one or more openings 74 through which bone can grow. The wedge member 36 may be hollow and contain material 130 which promotes the growth of bone through the wedge member.

A screw member 100 may extend ahead of the thin leading edge 44 of the wedge member 36 and engage hard cortical bone. Force may be transmitted from the screw member 100 to the wedge member 36 to move the wedge member relative to the bone. Alternatively, the wedge member 36 may have a circular cross sectional configuration with an external thread convolution 116 to enable the wedge member to be moved into an opening in a bone by rotating the wedge member.

I claim:

1. An apparatus assembly for use in association with bones of a patient, the apparatus assembly comprising:
a body constructed of a polymeric material including a thick end portion, a thin end portion defining a thin end axis that extends between first and second opposite ends, a first side portion having a first side surface, a second side portion having a second side surface, an upper surface and a lower surface, the thick end portion having a first thickness and the thin end portion having a second thickness, the first thickness being greater than the second thickness, the body further including a central opening extending generally vertically through the upper surface and the lower surface, the central opening having an internal surface including an internal leading surface, a first internal side surface and a second internal side surface, a maximum central opening width defined between the first and second internal side surfaces and substantially parallel to the thin end axis, the first internal side surface being spaced from the first side surface at a first spacing and the second internal side surface being spaced from the second side surface at a second spacing, the first spacing being substantially constant in the first side portion and the second spacing being substantially constant in the second side portion, the maximum central opening width being greater than a sum of the first spacing and the second spacing, the internal leading surface defining an internal leading height that is substantially constant between a first internal end and a second internal end of the internal leading surface; and
a mounting strip configured to abut the thick end portion, the mounting strip constructed of a metallic material, the mounting strip including a first screw hole and a second screw hole.

2. The apparatus assembly of claim 1, further comprising:
a first screw having a first head and a first threaded shaft; and
a second screw having a second head and a second threaded shaft, the first screw hole configured to receive the first screw at least partially therein and the second screw hole configured to receive the second screw at least partially therein in a mounted configuration, at least a portion of the first and second threaded shafts engaging hard cortical bone of the patient's bones in the mounted configuration.

3. The apparatus assembly of claim 2, wherein the first head is configured for engagement with the mounting strip proximate the first screw hole and the second head is configured for engagement with the mounting strip proximate the second screw hole in the mounted configuration.

4. The apparatus assembly of claim 1, wherein the first screw hole is positioned substantially above the upper surface and the second screw hole is positioned substantially below the lower surface in the mounted configuration, the thin end portion tapering to a thin edge.

5. The apparatus assembly of claim 1, wherein the central opening has a configuration which is similar to but smaller than the overall configuration of the body.

6. The apparatus assembly of claim 1, wherein the first spacing is substantially the same as the second spacing.

7. The apparatus assembly of claim 1, wherein the upper and lower surfaces define an acute angle.

8. The apparatus assembly of claim 7, wherein the acute angle is between one degree and twenty degrees.

9. The apparatus assembly of claim 1, wherein the mounting strip includes an upper portion extending above the upper surface and a lower portion extending below the lower surface.

10. The apparatus assembly of claim 1, wherein the body defines a maximum body width between the first side surface and the second side surface, the maximum central opening width being greater than one half the body width.

11. The apparatus assembly of claim 1, wherein the first side surface, the second side surface, the thick end portion and the thin end portion are generally continuous between the upper and lower surfaces to laterally enclose the central opening, the body comprising a wedge member.

12. The apparatus assembly of claim 1, wherein the body includes an internal trailing surface, the central opening defined by the internal trailing surface, the internal leading surface, the first internal side surface and the second internal side surface, the body being coated with a material that promotes growth of bone.

13. The apparatus assembly of claim 1, wherein the internal leading surface extends substantially parallel to the thin edge axis.

14. The apparatus assembly of claim 1, wherein the central opening is configured to be filled with bone growth inducing material for promoting growth of bone through the central opening.

15. An apparatus assembly for use in association with bones of a patient, the apparatus assembly comprising:
a body constructed of a polymeric material including a thick end portion, a thin end portion defining a thin end axis that extends between first and second opposite ends, a first side portion having a first side surface, a second side portion having a second side surface, an upper surface and a lower surface, the thick end portion having a first thickness and the thin end portion having a second thickness, the first thickness being greater than the second thickness, the body further including a central opening extending generally vertically through the upper surface and the lower surface, the central opening having an internal surface including an internal leading surface, a first internal side surface and a second internal side surface, a maximum central opening width defined between the first and second internal side surfaces and being measured substantially parallel relative to the thin end axis, the first internal side surface is spaced from the first side surface at a first spacing and the second internal side surface is spaced from the second side surface at a second spacing, the first and second spacings being substantially constant in the first side portion and the second side portion, respectively, the first spacing being substantially the same as the second spacing, the maximum central opening width being greater than a sum of the first spacing and the second spacing, the internal leading surface defining an internal leading height that is substantially constant between a first internal end and a second internal end of the internal leading surface, the thin end portion defining a leading edge and the thick end portion defining a trailing end, a body length defined between the leading edge and the trailing end, a body width defined between the first side surface and the second side surface substantially parallel to the thin end axis and measured proximate the maximum central opening width, the body width being greater than the body length;
a first screw;
a second screw; and
a mounting strip configured to abut the thick end portion in a mounted configuration, the mounting strip constructed of a metallic material, the mounting strip having a first screw hole and a second screw hole, the first screw hole configured to receive the first screw and the second screw hole configured to receive the second screw in the mounted configuration, the first and second screws spaced from the body in the mounted configuration.

16. The apparatus assembly of claim 15, wherein the first screw includes a first head and a first threaded shaft and the second screw includes a second head and a second threaded shaft, at least a portion of the first threaded shaft positioned above the upper surface and at least a portion of the second threaded shaft positioned below the lower surface in the mounted configuration.

17. The apparatus assembly of claim 15, further comprising:
a second mounting strip connected to the body; and
a third mounting strip connected to the body.

18. The apparatus assembly of claim 15, wherein the body is formed of a porous material, the body comprising a wedge member.

19. The apparatus assembly of claim 15, wherein the upper and lower surfaces define an acute angle.

20. The apparatus assembly of claim 19, wherein the acute angle is between one degree and twenty degrees.

21. The apparatus assembly of claim 15, wherein the body has a shape that is configured to substantially match the cross-sectional configuration of an outside surface of the bones at a location where the body is configured to be mounted.

22. The apparatus assembly of claim 15, wherein the first internal side surface is arcuate and the second internal side surface is arcuate.

23. The apparatus assembly of claim 15, wherein the internal surface includes an internal trailing surface, the central opening defined by the internal leading surface, the internal trailing surface and the first and second internal side surfaces.

24. The apparatus assembly of claim 15, wherein the mounting strip includes a front surface and a rear surface, the front surface in facing engagement with the thick end portion in the mounted configuration.

25. An apparatus assembly for use in association with bones of a patient, the apparatus assembly comprising:
a body including a thick end portion, a thin end portion, a first side portion, a second side portion, an upper surface and a lower surface, the thick end portion having a first thickness and the thin end portion having a second thickness, the first thickness being greater than the second thickness, the upper surface and the lower surface tapering toward each other from the thick end portion toward the thin end portion and defining an acute angle, the acute angle being in a range between one degree and twenty degrees, the first side portion having a first side surface and the second side portion having a second side surface, the body including an internal leading surface, an internal trailing surface, a first internal side surface and a second internal side surface, the second thickness being substantially constant between the first and second side surfaces proximate the internal leading surface, the body having a substantially straight leading edge along a front of the thin end portion at the upper surface extending between first and second opposite ends, a thin end axis extending between the first and second opposite ends, the internal leading surface positioned substantially parallel relative to the thin end axis, a first spacing defined between the first side surface and the first internal side surface and a second spacing defined between the second side surface and the second internal side surface, the first spacing being substantially equal to the second spacing, the first spacing being substantially constant in the first portion, a body width defined between the first side surface and the second side surface and a body length defined between the leading edge and a trailing surface of the thick end portion, the body width being greater than the body length;
a first mounting strip configured to abut the thick end portion, the mounting strip including a first screw hole and a second screw hole, the first mounting strip including an upper portion that extends above the upper surface in a mounted configuration; and a first screw including a first head and a first threaded shaft, the first screw configured for positioning at least partially in the first screw hole in the mounted configuration with the first threaded shaft at least partially engaging hard cortical bone of the patient's bones in the mounted configuration.

26. The apparatus assembly of claim 25, wherein the first side surface, the trailing surface and the second side surface are arcuate.

27. The apparatus assembly of claim 25, wherein the body is constructed of a polymeric material and the first mounting strip is constructed of a metallic material.

28. The apparatus assembly of claim 25, wherein the body includes a central opening defined by the internal trailing surface, the internal leading surface and the first and second internal side surfaces.

29. The apparatus assembly of claim 25, further comprising:

a second screw including a second head and a second threaded shaft, the second screw configured for positioning at least partially in the second screw hole in the mounted configuration with the second threaded shaft at least partially engaging hard cortical bone of the patient's bones in the mounted configuration.

30. The apparatus assembly of claim 25, further comprising:

a second mounting strip connected to the body, the second mounting strip constructed of a metallic material, the second mounting strip including a third screw hole.

* * * * *